(12) United States Patent
Kung et al.

(10) Patent No.: US 9,518,024 B2
(45) Date of Patent: Dec. 13, 2016

(54) METHOD AND SYSTEM FOR PREPARING CAPROLACTAM

(71) Applicant: China Petrochemical Development Corporation, Taipei (TW)

(72) Inventors: Yung-Shun Kung, Taipei (TW); Jih-Dar Hwang, Taipei (TW); Yao-Ching Tsai, Taipei (TW)

(73) Assignee: China Petrochemical Development Corporation, Taipei (TW)

( * ) Notice: Subject to any disclaimer, the term of this patent is extended or adjusted under 35 U.S.C. 154(b) by 0 days.

(21) Appl. No.: 14/996,723

(22) Filed: Jan. 15, 2016

(65) Prior Publication Data
US 2016/0237038 A1 Aug. 18, 2016

(30) Foreign Application Priority Data
Feb. 13, 2015 (TW) .............................. 104104987 A (51) Int. Cl.
*C07D 201/04* (2006.01)
*C07D 223/10* (2006.01)
*B01J 19/24* (2006.01)
*B01J 8/02* (2006.01)

(52) U.S. Cl.
CPC ................ *C07D 223/10* (2013.01); *B01J 8/02* (2013.01); *B01J 19/245* (2013.01); *B01J 2208/02* (2013.01); *B01J 2219/24* (2013.01)

(58) Field of Classification Search
CPC .................................................... C07D 201/04
See application file for complete search history.

(56) References Cited

U.S. PATENT DOCUMENTS

| 5,496,941 A * | 3/1996 | Ritz .................... C07D 201/16 540/539 |
| 6,677,449 B2 * | 1/2004 | Bassler ................ C07D 201/16 540/539 |
| 6,683,179 B2 * | 1/2004 | Bassler ................ C07D 201/08 540/539 |
| 7,217,818 B2 * | 5/2007 | Fischer ................ C07D 201/16 540/539 |
| 7,501,047 B2 * | 3/2009 | Luyken ................ C07D 201/16 203/35 |

* cited by examiner

*Primary Examiner* — Bruck Kifle
(74) *Attorney, Agent, or Firm* — Mintz Levin Cohn Ferris Glovsky and Popeo, P.C.; Steven M. Jenson; Richard B. Emmons (57) ABSTRACT

The present disclosure provides a method for preparing a caprolactam and the method includes steps of subjecting cyclohexanone oxime and sulfuric acid to a Beckmann rearrangement reaction to obtain a rearrangement mixture; neutralizing the rearrangement mixture and extracting the neutralized rearrangement mixture using an organic solvent sequentially; and subjecting the extracted organic solution to a hydrogenation reaction so as to simplify the process to produce a high quality caprolactam.

15 Claims, 7 Drawing Sheets

METHOD AND SYSTEM FOR PREPARING CAPROLACTAM

CROSS-REFERENCE TO RELATED APPLICATION

This application claims under 35 U.S.C. §119(a) the benefit of Taiwanese Patent Application No. 104104987 filed Feb. 13, 2015, the entire contents of which are incorporated herein by reference.

BACKGROUND

1. Technical Field

The present disclosure relates a method for preparing caprolactam, and more particularly to a method for preparing caprolactam with a simplified process.

2. Description of Related Art

Caprolactam is an important raw material for the production of nylon 6 fibers and resins. In order to produce high quality caprolactam to satisfy the production of Nylon-6 or polymerization of the resin, there are many purification steps in the traditional production process. These purification steps comprise an organic solvent extraction, alkaline washing, back-extraction of caprolactam solution with water (water-back-extraction), steam stripping of removing organic solvent, ion exchange, and hydrogenation reactions, and finally the process is completed with evaporation and distillation steps to produce a high quality caprolactam. For example, to produce caprolactam in the industry, U.S. Pat. No. 7,700,767 discloses, under the oleum-catalyzed condition, cyclohexanone oxime was subjected to Beckmann rearrangement reaction, then the reaction mixture was neutralized with ammonia and subsequently was subjected to solvent extraction with benzene. The organic phase portion of benzene was collected, then undergone alkaline washing and water-back-extraction. Benzene was removed by steam stripping to obtain an aqueous solution of caprolactam with a concentration of about 30 to 40 wt %. The process was followed by ion exchange treatment system to remove inorganic salt impurities in caprolactam aqueous solution. Later, with the presence of hydrogen and a nickel-containing catalyst, unsaturated organic impurities in the caprolactam aqueous solution was reacted with hydrogen. Finally, the caprolactam solution was evaporated and distillated to obtain caprolactam products.

European Patent No. 411,455 discloses a continuous caprolactam purification method using cyclohexanone oxime subjected to Beckmann rearrangement, neutralization with ammonia, solvent extraction of benzene, steam stripping to remove the organic solvent, and other traditional manufacturing processes, and finally an aqueous solution form of caprolactam was subjected to the three-phase (vapor-liquid-solid) hydrogenation fixed bed operating system. In addition, U.S. Pat. No. 5,539,106 discloses a hydrogenation purification method for a caprolactam-water mixture, in which the caprolactam-water mixture is first contacted with the gaseous hydrogen, followed by contacting a hydrogenation catalyst for hydrogenation purification in a fixed bed.

It can be seen that, in the existing hydrogenation steps of the caprolactam manufacturing method, an aqueous solution of caprolactam is used for the reaction. Therefore, the steps of water-back-extraction are necessary to remove organic solvents in the aqueous solution. It consumes large amounts of steam energy. Moreover, ion exchange step which is carried out prior to the hydrogenation reaction in conventional manufacturing process requires frequent replacement and regeneration of ion exchange resins with increased production cost and the subsequent waste-water treatment problems.

Therefore, how to simplify the manufacturing process to produce high-quality caprolactam has become the issue to be resolved anxiously.

SUMMARY

The present disclosure provides a method for preparing caprolactam that performs a hydrogenation reaction using an organic solution containing caprolactam. In addition, in the preparation method of the present disclosure, after cyclohexanone oxime and sulfuric acid are subjected to a Beckmann rearrangement reaction to obtain a rearrangement mixture, it is adequate to merely perform neutralization reaction, organic solvent extraction and alkaline washing prior to performing the hydrogenation reaction using an organic solution containing caprolactam. In one embodiment, the caprolactam organic solution is treated by evaporation and distillation to obtain caprolactam products. As compared to existing prior art, the traditional steps of water-back-extraction and ion exchange are simplified to reduce a large amount of steam consumptions and to resolve the subsequent waste-water treatment problems. The simplified method for preparing caprolactam of the present disclosure can produce high-purity caprolactam.

In one embodiment, the present disclosure provides a method for preparing caprolactam comprising steps of:

(a) subjecting cyclohexanone oxime and sulfuric acid to a Beckmann rearrangement reaction to obtain a rearrangement mixture;

(b) neutralizing the rearrangement mixture with a base to obtain a first crude caprolactam solution rich in caprolactam and a second crude caprolactam solution rich in sulfate;

(c) extracting at least the first crude caprolactam solution with an organic solvent to obtain a caprolactam organic solution;

(d) mixing the caprolactam organic solution with hydrogen to perform a hydrogenation reaction in a hydrogenation reactor having a hydrogenation catalyst, wherein a weight hourly space velocity (WSHV) of the caprolactam organic solution is 1 to 20 per hour, a feeding hydrogen flow rate is 0.01 to 0.15 $NM^3$ per hour per cubic meter of the caprolactam organic solution, and a hydrogen gauge pressure of an outlet of the hydrogenation reactor is 3 to 20 $kg/cm^2$; and (e) purifying the hydrogenated caprolactam organic solution.

In one embodiment, the method for preparing caprolactam of the present disclosure further comprises extracting the second crude caprolactam solution with the organic solvent to obtain the caprolactam organic solution. The organic solvent can be used to extract the first crude caprolactam solution and the second crude caprolactam solution at the same time, or to extract the first crude caprolactam solution and the second crude caprolactam solution, respectively.

In one embodiment, the organic solvent for extraction in the present disclosure is an aromatic hydrocarbon or a halogenated hydrocarbon.

In another embodiment, the organic solvent for extraction in the present disclosure is toluene, benzene or dichloroethane.

In one embodiment, the base for the neutralization reaction in the present disclosure is ammonia.

In one embodiment, the method for preparing caprolactam of the present disclosure further comprises adjusting the electric conductivity of the caprolactam organic solution to 5 to 100 μmoh/cm with a base aqueous solution after the step (c).

In still another embodiment, the method for preparing caprolactam of the present disclosure further comprises removing at least a portion of the organic solvent after the step (c).

In one embodiment, the hydrogenation catalyst for the hydrogenation reaction of the present disclosure comprises a carrier and an active metal carried on the carrier, wherein the carrier is one selected from the group consisting of alumina, carbon and silica.

In one embodiment, the active metal is one selected from the group consisting of ruthenium, rhodium, palladium, platinum and nickel. Further, an amount of the active metal is 5 to 85 wt %.

In one embodiment, an amount of the nickel is 5 to 85 wt %.

In one embodiment, the reaction temperature of the hydrogenation reaction of the present disclosure is 50 to 180° C.

In one embodiment, the method for preparing caprolactam of the present disclosure further comprises adding at least one alkali metal hydroxide in the hydrogenated caprolactam organic solution, prior to or during the step (e).

The present disclosure further provides a system for preparing caprolactam comprising: a reaction unit configured to subject cyclohexanone oxime and sulfuric acid to a Beckmann rearrangement reaction to obtain a rearrangement mixture; a neutralization unit connected with the reaction unit and configured to receive the rearrangement mixture from the reaction unit, wherein the neutralization unit contains a base to perform a neutralization reaction with the rearrangement mixture to obtain a first crude caprolactam solution rich in caprolactam and a second crude caprolactam solution rich in sulfate; an extraction unit connected to the neutralization unit and configured to receive at least the first crude caprolactam solution from the neutralization unit, wherein the extraction unit contains an organic solvent to extract at least the first crude caprolactam solution to obtain a caprolactam organic solution; a hydrogenation unit connected to the extraction unit and configured to receive the caprolactam organic solution from the extraction unit, wherein the hydrogenation unit comprises hydrogen and a fixed bed, and a hydrogenation catalyst is disposed on the fixed bed to subject the caprolactam organic solution and hydrogen to a hydrogenation reaction, and wherein a weight hourly space velocity (WSHV) of the caprolactam organic solution is 1 to 20 per hour, a feeding hydrogen flow rate is 0.01 to 0.15 $NM^3$ per hour per cubic meter of the caprolactam organic solution, and a hydrogen gauge pressure of an outlet of the hydrogenation reaction is 3 to 20 $kg/cm^2$; and a purification unit connected to the hydrogenation unit and configured to receive the hydrogenated caprolactam organic solution from the hydrogenation unit, wherein the purification unit comprises an evaporation device and a distillation device.

In one embodiment, the system for preparing caprolactam of the present disclosure further comprises a first temporary storage unit connected with the extraction unit and the hydrogenation unit, and configured to receive the caprolactam organic solution from the extraction unit, wherein the electric conductivity of the caprolactam organic solution is adjusted to 5 to 100 μmoh/cm with a base aqueous solution.

In another embodiment, the system for preparing caprolactam of the present disclosure further comprises a first concentration unit connected with the extraction unit and the hydrogenation unit, and configured to receive the caprolactam organic solution from the extraction unit, with at least a portion of the organic solvent being removed.

In another embodiment, the system for preparing caprolactam of the present disclosure further comprises a second temporary storage unit and a second concentration unit connected with the temporary storage unit, and the temporary storage unit, wherein the second temporary storage unit and the second concentration unit are disposed sequentially after the extraction unit, and wherein the concentration unit is connected with the hydrogenation unit.

Further, in one embodiment, the system for preparing caprolactam of the present disclosure further comprises a third temporary storage unit connected with the hydrogenation unit and the purification unit to receive the hydrogenated caprolactam organic solution from the hydrogenation unit, with at least one alkali metal hydroxide added to the hydrogenated caprolactam organic solution.

It can be realized from the above that the method and system thereof for preparing caprolactam of the present disclosure is based on a novel hydrogenation method by eliminating the steps of water-back-extraction, solvent steam stripping, and ion exchange treatment in the conventional processes. It reduces energy consumptions of the steam stripping and usage of aqueous solution. It also does not require to replace ion exchange resins without increasing the cost for the subsequent waste-water treatment. Compared to the lengthy steps of the conventional processes associated with the issues of significant consumption of steam energy, the method for preparing caprolactam and system thereof of the present disclosure not only produce a high quality of caprolactam, but also have advantages of energy-saving and simplified process.

DETAILED DESCRIPTION OF THE PREFERRED EMBODIMENTS

The following specific examples are used for illustrating the present disclosure. A person skilled in the art can easily conceive the other advantages and effects of the present disclosure based on the disclosure of this specification.

The present disclosure provides a method for preparing caprolactam comprising the following steps (a) subjecting cyclohexanone oxime and sulfuric acid to a Beckmann rearrangement reaction to obtain a rearrangement mixture;

(b) neutralizing the rearrangement mixture with a base to obtain a first crude caprolactam solution rich in caprolactam and a second crude caprolactam solution rich in sulfate;

(c) extracting at least the first crude caprolactam solution with an organic solvent to obtain a caprolactam organic solution;

(d) mixing the caprolactam organic solution with hydrogen to perform a hydrogenation reaction in a hydrogenation reactor having a hydrogenation catalyst, wherein a weight hourly space velocity of the caprolactam organic solution is 1 to 20 per hour, a feeding hydrogen flow rate is 0.01 to 0.15 $NM^3$ per hour per cubic meter of the caprolactam organic solution, and a hydrogen gauge pressure of an outlet of the hydrogenation reactor is 3 to 20 $kg/cm^2$; and (e) purifying the hydrogenated caprolactam organic solution.

To implement the method for preparing caprolactam of the present disclosure, the present disclosure further provides a system for preparing caprolactam comprising a reaction unit, a neutralization unit, an extraction unit, a hydrogenation unit and a purification unit.

Figure 1:
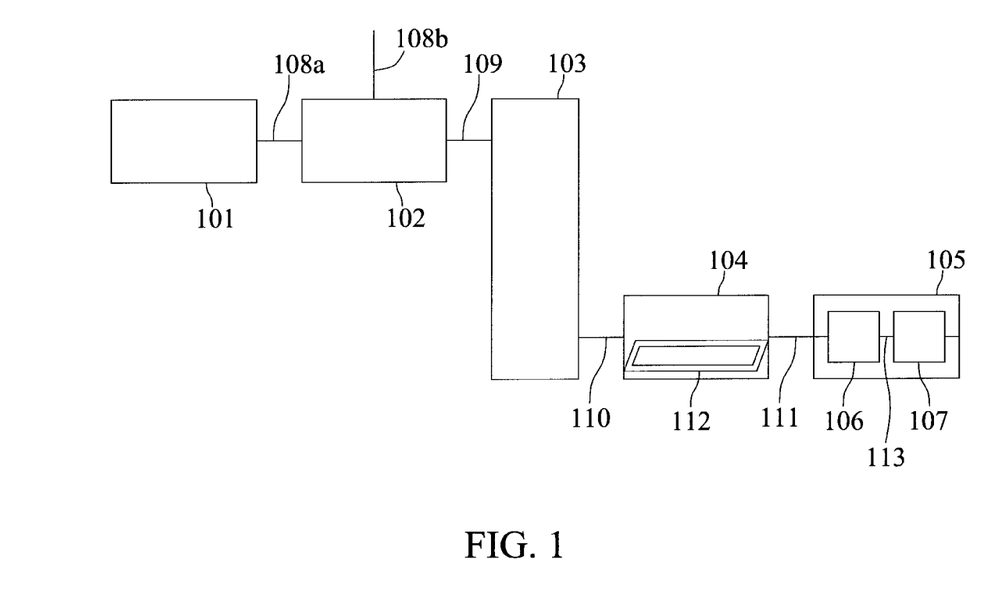
FIG. 1 is a schematic diagram illustrating the system for preparing caprolactam.

As shown in FIG. 1, it is a schematic diagram illustrating the system for preparing caprolactam of the present disclosure. The system comprises a reaction unit 101; a neutralization unit 102 which is connected to the reaction unit 101 via a pipe 108a, wherein the neutralization unit 102 is connected with additional pipe 108b; an extraction unit 103 which is connected to the neutralization unit 102 via a pipe 109; a hydrogenation unit 104 which is connected to the extraction unit 103 via a pipe 110; and a purification unit 105 which is connected to the hydrogenation unit 104 via a pipe 111.

According to the above system for preparing caprolactam, the hydrogenation unit 104 has a fixed bed 112, and a hydrogenation catalyst (not shown) is fixed on the fixed bed 112. Further, the purification unit 105 comprises an evaporation device 106 and a distillation device 107.

Moreover, in one example, the evaporation device 106 can be selected from a multi-effect evaporation device or a vapor re-compression evaporation device. The distillation device 107 can be commonly used distillation column, and the evaporation device 106 is connected with the distillation device 107 via a pipe 113.

In the step (a), according to the conventional art, the cyclohexanone oxime is subjected to a Beckmann rearrangement reaction in the reaction unit 101 under the catalysis of sulfuric acid to produce a rearrangement mixture.

Then, the rearrangement mixture is fed from the reaction unit 101 into the neutralization unit 102 via the pipe 108a. In the step (b), the pipe 108b delivers a base to the neutralization unit 102 which allows the base and the rearrangement mixture to perform a neutralization reaction to obtain a first crude caprolactam solution rich in caprolactam and a second crude caprolactam solution rich in sulfate, wherein the commonly used base is ammonia and the obtained sulfate is ammonium sulfate accordingly. The neutralization reaction with the usage of ammonia allows the formation of ammonium sulfate derived from sulfuric acid. After completion of the neutralization reaction, it allows the formation of the first crude caprolactam solution rich in caprolactam in the upper layer and the formation of the second crude caprolactam solution rich in sulfate with small amount of caprolactam in the under layer. The term "first crude caprolactam solution rich in caprolactam" as used herein refers that the amount of caprolactam is more than 50 wt %. The term "second crude caprolactam solution rich in sulfate" as used herein refers that the amount of sulfate is more than that of caprolactam. Further, the amount of caprolactam in the first crude caprolactam solution rich in caprolactam is about 68 to 75 wt %, in which there are additional organic and inorganic impurities. The pH value of the aqueous solution is 4.0 to 6.0.

In the step (c), the first crude caprolactam solution is extracted at least with the organic solvent to obtain the caprolactam organic solution. As shown in FIG. 1, the extraction unit 103 is connected to the neutralization unit 102, and the pipe 109 receives the first crude caprolactam solution fed from the neutralization unit 102, and the extraction unit 103 has the organic solvent so as to extract at least the first crude caprolactam solution to obtain the caprolactam organic solution.

Figure 2:
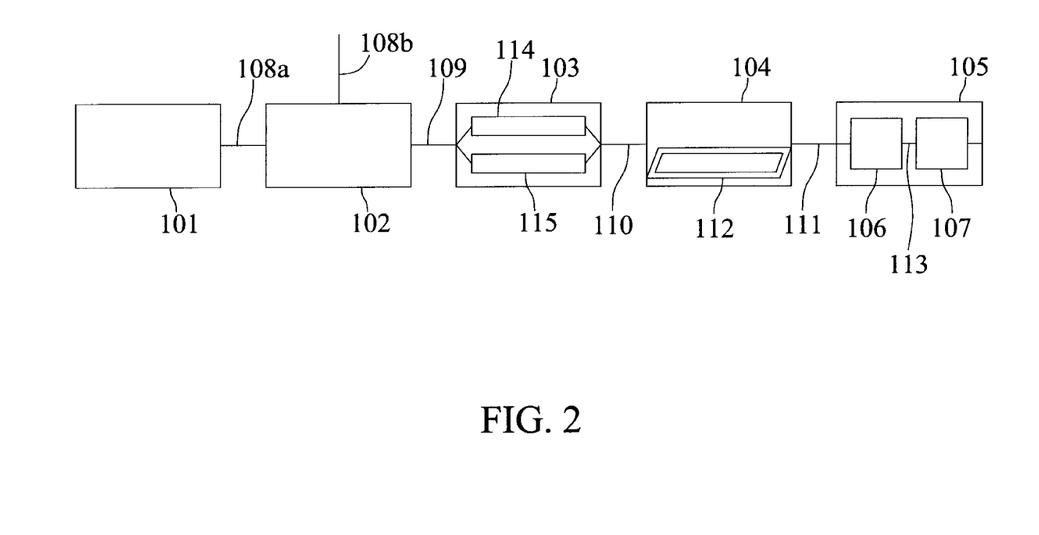
FIG. 2 is a schematic diagram illustrating the extraction units of the system for preparing caprolactam in parallel-connection extraction.

In one embodiment, the method for preparing caprolactam of the present disclosure further comprises a step of extracting the second crude caprolactam solution with the organic solvent to obtain a second caprolactam organic solution. The organic solvent can simultaneously extract the first crude caprolactam solution and the second crude caprolactam solution in series mode or in parallel mode. Also as shown in FIG. 2, the extraction unit 103 has chambers 114 and 115 for extracting the first crude caprolactam solution and the second crude caprolactam solution in parallel mode, respectively.

According to the above step (c), the extraction unit 103 used for the extraction is not particularly limited. The examples of the extraction unit 103 include, but not limited to, at least one selected from the group consisting of packed column, plate column, pulse column, rotary disc column and vibratory column.

According to the above method, the organic solvent used for the extraction is not particularly limited. The examples of the organic solvent include, but not limited to, at least one selected from the group consisting of toluene, benzene and ethylene dichloride.

In one embodiment, the method for preparing caprolactam of the present disclosure further comprises a step of adjusting the electric conductivity of the caprolactam organic solution with water or an aqueous solution containing a base after the step (c) and prior to the hydrogenation. The electric conductivity is controlled at 5 to 100 μmoh/cm, preferably 5 to 40 μmoh/cm. The usage of water or the aqueous solution containing the base is 0.01 to 0.5 times of the volume of caprolactam organic solution, preferably 0.01 to 0.1 times of the volume of caprolactam organic solution, wherein the examples of the base aqueous solution are not particularly limited. The example of the base aqueous solution includes a solution of an alkali metal, such as sodium hydroxide solution.

Figure 3:
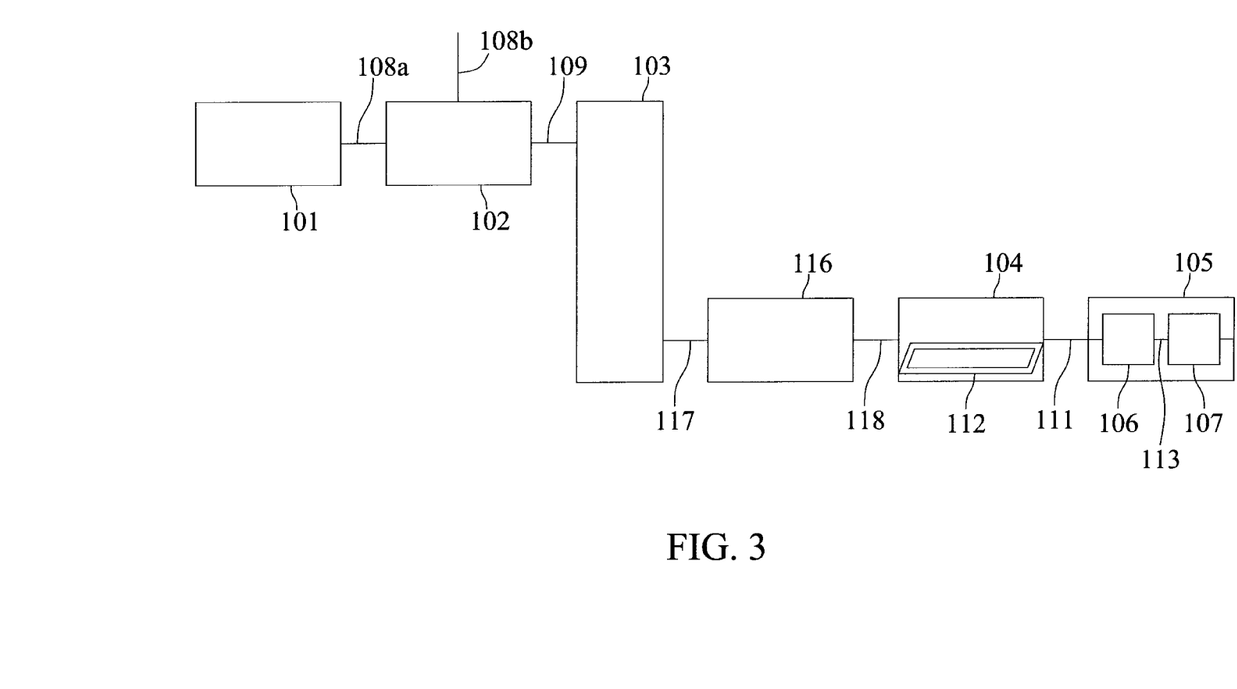
FIG. 3 is a schematic diagram illustrating the system for preparing caprolactam that further comprises a temporary storage unit.

According to the above embodiment, as the aspect shown in FIG. 3, it is corresponding to the system for preparing caprolactam of the present disclosure. The system for preparing caprolactam further comprises a temporary storage unit 116, which is connected with the extraction unit 103 and the hydrogenation unit 104, and the pipe 117 receives the caprolactam organic solution fed from the extraction unit 103, and then the caprolactam organic solution with adjusted electric conductivity is discharged into the hydrogenation unit 104 via the pipe 118.

Figure 4:
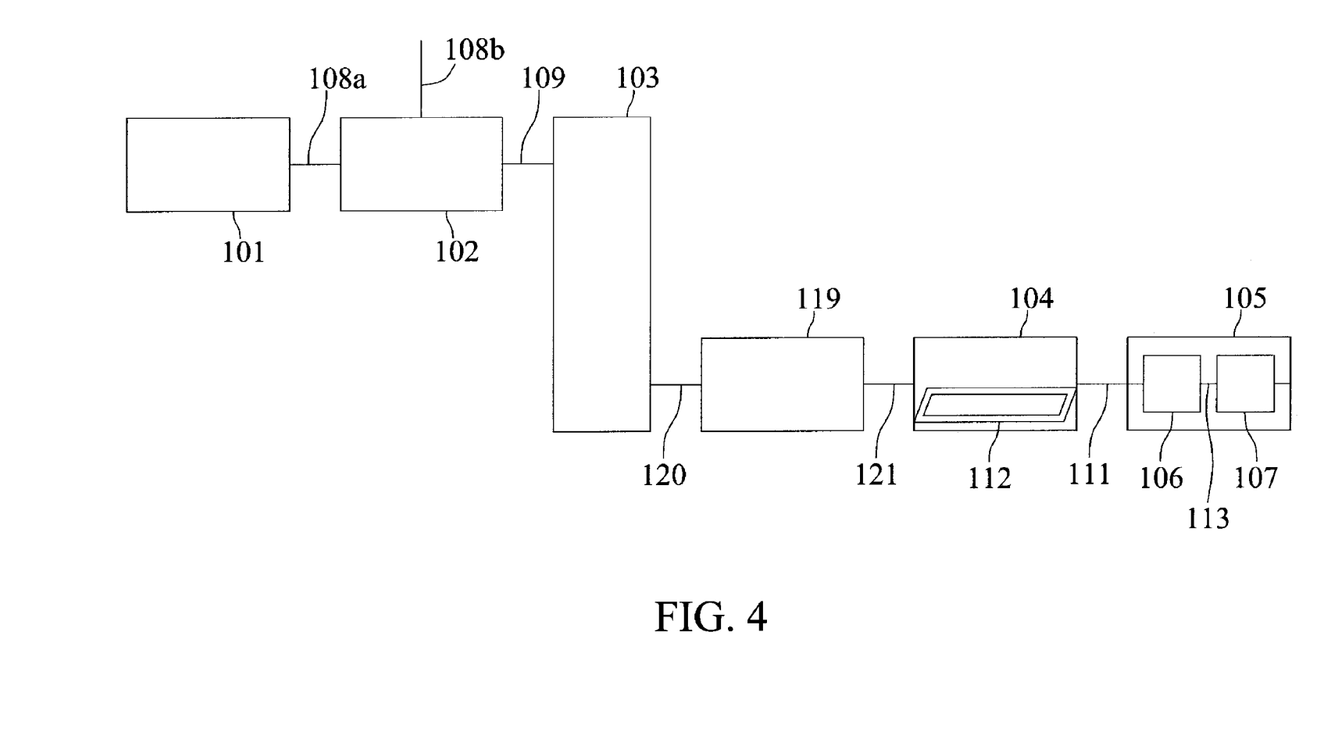
FIG. 4 is a schematic diagram illustrating the system for preparing caprolactam that further comprises a concentration unit.
Figure 5:
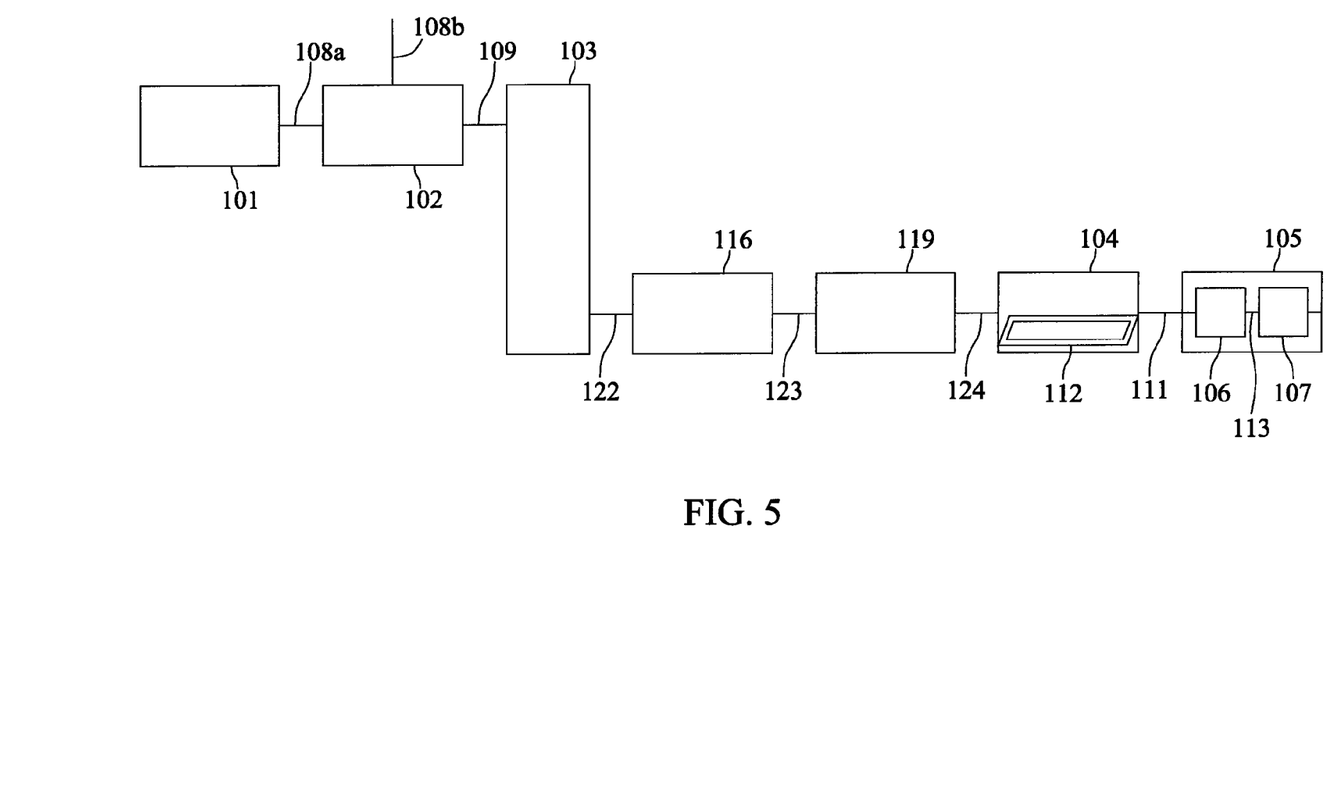
FIG. 5 is a schematic diagram illustrating the system for preparing caprolactam that further comprises a temporary storage unit and a concentration unit.

In still one embodiment, the method for preparing caprolactam of the present disclosure further comprises a step of removing at least a portion of the organic solvent after the step (c). As the aspect shown in FIG. 4, the system for preparing caprolactam further comprises a concentration unit 119, which is connected with the extraction unit 103 and the hydrogenation unit 104, and the caprolactam organic solution fed from the extraction unit 103 is received via the pipe 120, and then the concentrated caprolactam organic solution is fed into the hydrogenation unit 104 via the pipe 121. The system for preparing caprolactam of the present disclosure is not limited to the above embodiments. The system for preparing caprolactam of the present disclosure can further comprise the temporary storage unit 116 and the concentration unit 119 at the same time, and the extraction unit 103 can be selected from the series extraction or the parallel extraction with the chambers 114 and 115 without particular limitation. As the aspect shown in FIG. 5, the system for preparing caprolactam of the present disclosure comprises the temporary storage unit 116 and the concentration unit 119 connected with the temporary storage unit 116, and the temporary storage unit 116 and the concentration unit 119 are disposed sequentially after the extraction unit 103, and the concentration unit 119 is connected with the hydrogenation unit 104, wherein the temporary storage unit 116 receives the caprolactam organic solution fed from the extraction unit 103 via the pipe 122, and the concentration unit 119 receives the caprolactam organic solution fed from the temporary storage unit 116 via the pipe 123, and the concentrated caprolactam organic solution is fed into the hydrogenation unit 104 via the pipe 124.

In the present disclosure, the steps of water-back-extraction, solvent steam stripping, and ion exchange treatment in the conventional process are eliminated. In the step (d), the hydrogenation of the extracted caprolactam organic solution is directly performed with hydrogen, wherein, as the aspect shown in FIG. 1, the hydrogenation unit 104 used for the hydrogenation is connected to the extraction unit 103 via the pipe 110, and the caprolactam organic solution in the extraction unit 103 is received via the pipe 110, and the hydrogenation catalyst is fixed on the fixed bed 112 of the hydrogenation unit 104.

In one embodiment, the hydrogenation unit 104 is not particularly limited and can be selected from a trickle-bed reactor and a bubbling reactor.

In the step (d), as mentioned above, the concentration of the extracted caprolactam organic solution used in the present disclosure is not particularly limited. The concentration unit 119 can be optionally used for removing the organic solvent to increase the concentration of the caprolactam organic solution. The concentration of the caprolactam organic solution is preferably 10 to 80 wt %.

In one example, a weight hourly space velocity of the caprolactam organic solution is 1 to 20 per hour, more preferably 1 to 15 per hour.

In one embodiment, a feeding hydrogen flow rate is 0.01 to 0.15 $NM^3$ per hour per cubic meter of the caprolactam organic solution, and a hydrogen gauge pressure of an outlet of the hydrogenation reactor is 3 to 20 $kg/cm^2$.

The hydrogenation catalyst of the present disclosure is consisting of a metal and a carrier. In one embodiment, the carrier of the hydrogenation catalyst is one selected from the group consisting of alumina, carbon and silica. The metal of the hydrogenation catalyst is one selected from the group consisting of ruthenium, rhodium, palladium, platinum and nickel. The metal amount of the hydrogenation catalyst is 5 to 85 wt %, more preferably 15 to 60 wt %.

In one example, the nickel amount of the hydrogenation catalyst is 5 to 85 wt %.

In one embodiment, temperature of the hydrogenation of the present disclosure is 50 to 180° C., preferably 50 to 150° C., more preferably 80 to 120° C.

After that, in the step (e), the hydrogenated caprolactam organic solution is purified, wherein the purification includes steps of evaporation and distillation to separate the caprolactam. The evaporated organic solution can be recovered to a solvent recovery system for recycling. As the aspect shown in FIG. 1, the purification unit 105 used for the purification is connected to the hydrogenation unit 104 via the pipe 111, and the caprolactam organic solution in the hydrogenation unit 104 is fed into the purification unit 105 via the pipe 111.

In one example, the purification unit 105 comprises the evaporation device 106 and the distillation device 107. Further, the evaporation device 106 can be selected from a multi-effect evaporation device or a vapor re-compression evaporation device. The distillation device 107 can be a commonly used distillation column.

In the step (e), the distillation step of the purification is operated at less than 50 mmHg vacuum levels, preferably 20 mmHg, and more preferably 10 mmHg. The temperature of the bottom of the boiler is set at 100 to 220° C., preferably 100 to 180° C., more preferably 100 to 150° C. For the distillation, light impurities with the boiling point less than the caprolactam initially are distilled under a low degree of vacuum, while the caprolactam is distilled under a higher degree of vacuum. The remaining residues at the bottom of the distillation unit are ionic impurities, amino acid alkali salts, organic impurities with a high boiling point, and etc.

In one embodiment, at least one of alkali metal hydroxide can be further added into the hydrogenated caprolactam organic solution prior to the purification or during the purification, such that helps to reduce the aggregation phenomena occurred during the distillation process and to enable a portion of impurities in the solution to form the amino acid salts which can be easily removed from the distillation system.

Figure 6:
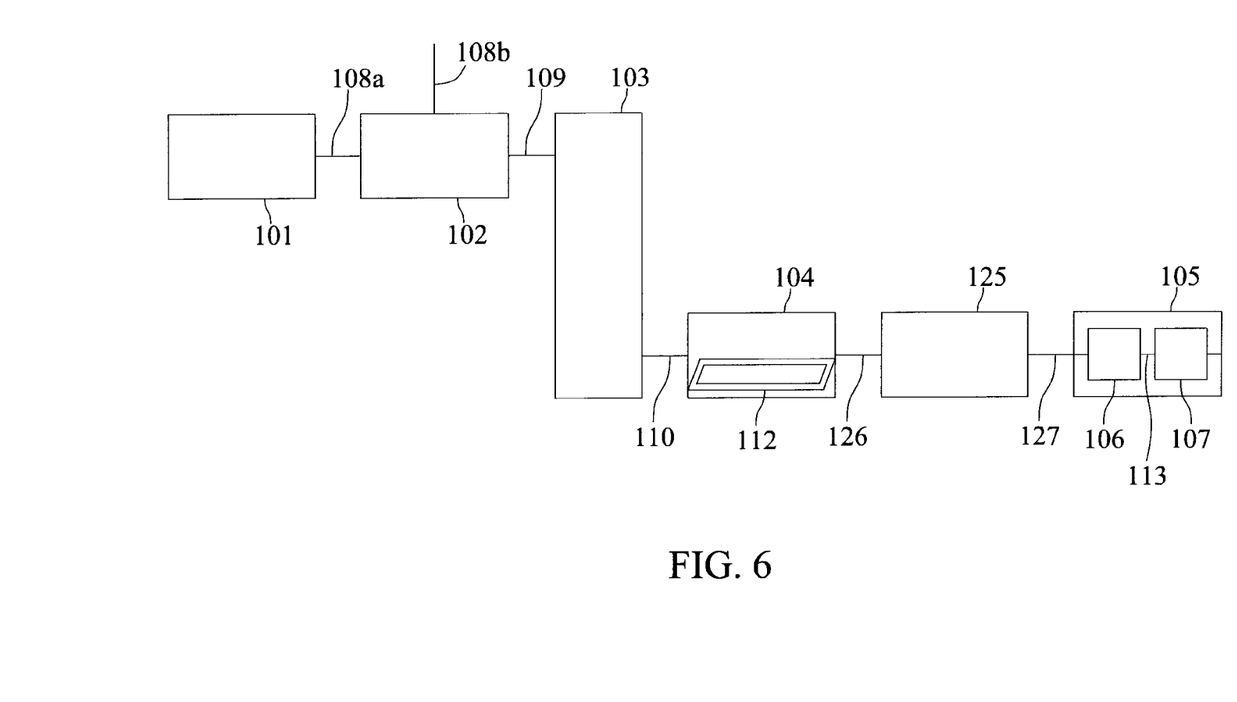
FIG. 6 is a schematic diagram illustrating the system for preparing caprolactam that further comprises a temporary storage unit according to another embodiment.

According to the above examples, as the aspect shown in FIG. 6, the system for preparing caprolactam of the present disclosure further comprises a temporary storage unit 125 which is connected to the hydrogenation unit 104 via the pipe 126, and the caprolactam organic solution in the hydrogenation unit 104 is fed via the pipe 126, and then the caprolactam organic solution is fed into the purification 105 via the pipe 127.

Figure 7:
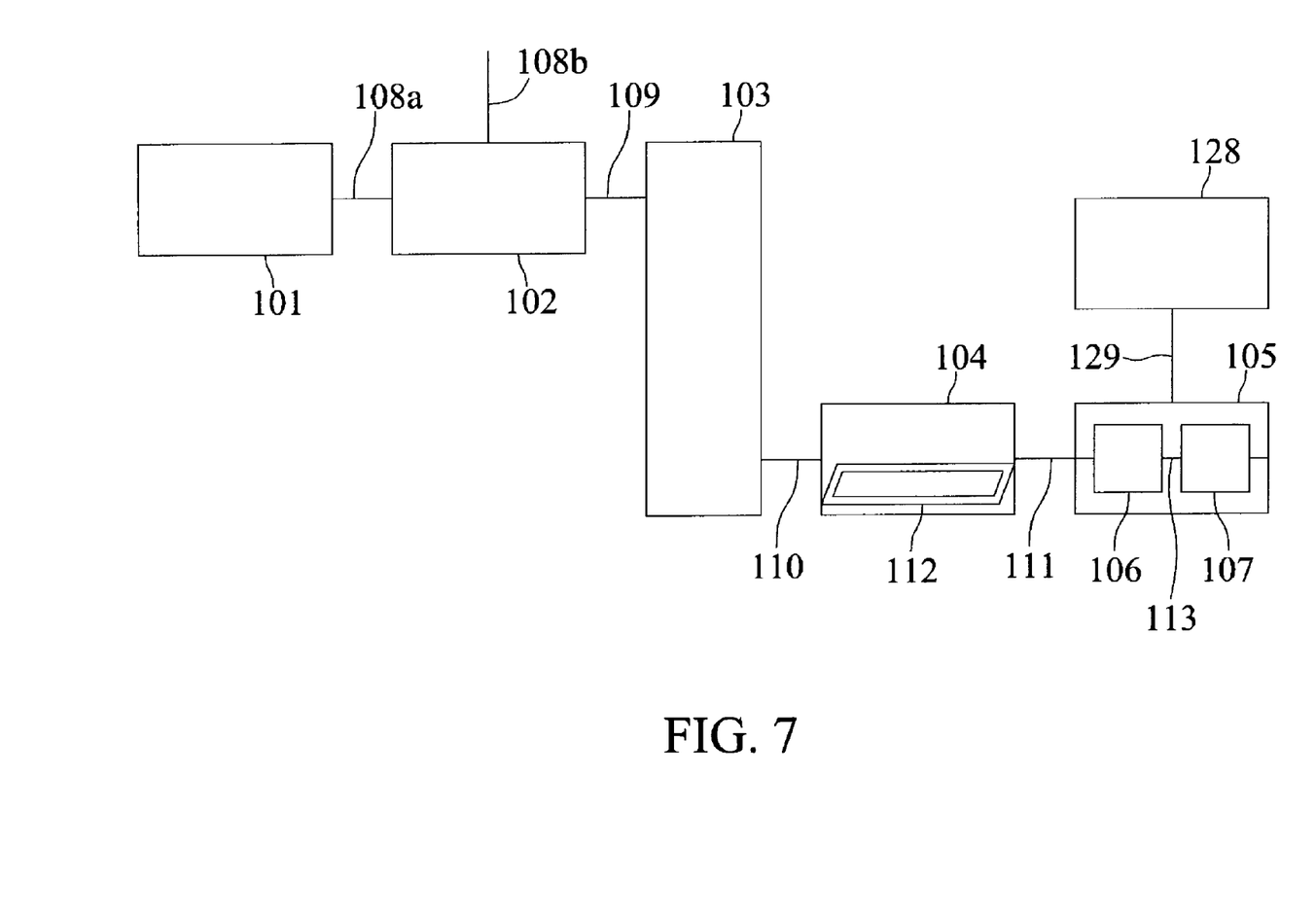
FIG. 7 is a schematic diagram illustrating the system for preparing caprolactam that further comprises a temporary storage unit according to still another embodiment.

In another aspect, as the aspect shown in FIG. 7, the system for preparing caprolactam of the present disclosure further comprises a temporary storage unit 128 which is connected to the purification unit 105 via the pipe 129, and at least one of alkali metal hydroxide is added via the pipe 129.

The system for preparing caprolactam of the present disclosure is not limited to the above examples. The temporary storage unit 125 of FIG. 6 or the temporary storage unit 128 of FIG. 7 can be present in the system for preparing caprolactam with the temporary storage unit 116 of FIG. 3 or the concentration unit 119 of FIG. 4 at the same time. Also, the system can comprise the temporary storage unit 116 and the concentration unit 119 at the same time, and also are present with the temporary storage unit 125 or the temporary storage unit 128 simultaneously. It is not particularly limited.

At the same time, the extraction unit 103 can be selected from the series extraction or the parallel extraction with the chambers 114 and 115, and it is not particularly limited.

According to the above examples, the alkali metal hydroxide is at least one selected from the group consisting of sodium hydroxide and potassium hydroxide, preferably sodium hydroxide. The amount of the alkali metal hydroxide is no more than 20 milliequivalent/per kilogram of the caprolactam organic solution, preferably 1 to 10 milliequivalent/per kilogram of the caprolactam organic solution.

EXAMPLES

According to the aforementioned conventional manufacturing process, cyclohexanone oxime and sulfuric acid were subjected to a Beckmann rearrangement reaction, and then followed by neutralization reaction with ammonia. Then the aqueous solution rich in crude caprolactam and ammonium sulfate solution containing small amounts of caprolactam were pumped into the extraction column, respectively, and contacted with benzene solvent. Two streams of caprolactam organic solutions were brought together, and washed with base and water. The conductivity of the caprolactam organic solution after washing was 54 μmoh/cm, a caprolactam benzene solution with a concentration of 25.3 wt % was obtained, and the caprolactam benzene solution contained 1.25 wt % of water. This caprolactam benzene solution was used as the source of the caprolactam organic solution for the following examples and comparative examples to carry out the subsequent steps.

Example 1

The caprolactam benzene solution with a concentration of 25.3 wt % was introduced to the hydrogenation reactor with a fluid dispenser on the top by a quantitative pump. A hydrogenation catalyst containing nickel was fixed on the fixed bed, and the nickel amount was 40 wt %. The weight hourly space velocity of the caprolactam benzene solution was set to 4.0 per hour, while a hydrogen gauge pressure of an outlet of the hydrogenation reactor was set to 5.5 kg/cm$^2$, and the feeding hydrogen flow rate was set to less than 0.05 NM$^3$ per hour per cubic meter of the caprolactam benzene solution, and the hydrogenation temperature was set to 90° C.

Next, sodium hydroxide was added to the hydrogenated caprolactam benzene solution that was equivalent to 8 mEq of sodium hydroxide per kg of caprolactam benzene solution. It was followed by solvent concentration treatment using concentrating machine with reduced pressure. The light impurities were removed by distillation with a degree of vacuum of 10 to 15 mmHg Finally, caprolactam was distilled with high level of vacuum of 3 to 10 mmHg. The volatile alkali, alkalinity, potassium permanganate number (PM), potassium permanganate absorption number (PAN), extinction value, and chroma of the distilled caprolactam were measured and recorded in Table 1.

Example 2

The procedure of example 1 was repeated, but the hydrogenation temperature was controlled to 70° C. The distilled caprolactam was measured, and the results were recorded in Table 1.

Example 3

The caprolactam benzene solution with a concentration of 25.3 wt % was concentrated under reduced pressure to obtain a caprolactam benzene solution with a concentration of 50.1 wt %, and then was fed into the hydrogenation reactor, and the procedure of example 1 was repeated, but the weight hourly space velocity of the caprolactam benzene solution was set to 7.55 per hour. The distilled caprolactam was measured, and the results were recorded in Table 1.

Comparative Example 1

Sodium hydroxide (equivalent to 8 mEq of sodium hydroxide per kg of caprolactam benzene solution) was added to the caprolactam benzene solution with a concentration of 25.3 wt % which was not treated by the hydrogenation, and then the solution was concentrated using reduced pressure machine for the solvent concentration treatment. The light impurities were removed by distillation with a vacuum degree of 10 to 15 mmHg Finally, caprolactam was distilled with a high vacuum degree of 3 to 10 mmHg. The distilled caprolactam was measured, and the results were recorded in Table 1.

Comparative Example 2

The caprolactam benzene solution with a concentration of 25.3 wt % was subjected to a step of water-back-extraction, and the benzene solution in the aqueous solution was removed by a steam stripping process. An aqueous solution of caprolactam with a concentration of 39.2 wt % was obtained.

The caprolactam solution was not subjected to the ion exchange and hydrogenation reaction. The sodium hydroxide (equivalent to 8 mEq sodium hydroxide per kg of caprolactam solution) was added directly into the caprolactam benzene solution, and then water was removed as concentration treatment using the concentrating machine with reduced pressure. The light impurities were removed by distillation with a vacuum degree of 10 to 15 mmHg Finally, the caprolactam was distilled with a high level of vacuum of 3 to 10 mmHg. The distilled caprolactam was measured, and the results were recorded in Table 1.

Comparative Example 3

The caprolactam benzene solution with a concentration of 25.3 wt % was subjected to a step of water-back-extraction, and the benzene solution in the aqueous solution was removed by the steam stripping process. An aqueous solution of caprolactam with a concentration of 39.2 wt % was obtained.

The caprolactam solution was not subjected to the ion exchange treatment, but it was treated by the hydrogenation. The weight hourly space velocity of the caprolactam solution was set to 7.55 per hour. Sodium hydroxide (equivalent to 8 mEq of sodium hydroxide per kg of caprolactam solution) was added to the caprolactam solution after the hydrogenation process. Water removing of the concentration treatment was performed using the concentrating machine with reduced pressure. The light impurities were removed by distillation with a vacuum degree of 10 to 15 mmHg Finally, caprolactam was distilled with a high level of vacuum of 3 to 10 mmHg. The distilled caprolactam was measured, and the results were recorded in Table 1.

Measurement

Detection methods used are described below:

Potassium permanganate absorption number (PAN) was measured according to ISO 8660. PAN number of caprolactam was a measurement of the amount of the impurities which can be oxidized in the caprolactam, and the higher PAN number indicated the presence of a higher amount of impurities which can be oxidized.

The measurement of potassium permanganate number (PM)—oxidative capacity was performed as follows: At 20 t, 3 grams (g) of caprolactam and 1 mL of 0.002 mol/L of potassium permanganate solution were added to 100 ml of pure water, and the time that was required to reduce the color intensity of the solution to equivalent to the color intensity of the standard solution was measured, starting from the addition of caprolactam and potassium permanganate solution. In which, the standard solution contained 3000 mg of cobalt nitrate and 12 mg of potassium dichromate in 1 liter (L) of pure water. The higher PM number indicated the presence of smaller amounts of impurities which can be oxidized.

Extinction value was measured according to ISO 7059. Chroma was measured according to ISO 8112.

TABLE 1

Caprolactam analysis of examples 1 to 3 and comparative examples 1 to 3

| | PM (sec) | PAN | Extinction value (290 nm) | Chroma |
|---|---|---|---|---|
| Example 1 | 32000 | 3.13 | 0.023 | <1 |
| Example 2 | 27000 | 3.39 | 0.022 | <1 |
| Example 3 | 35000 | 2.98 | 0.026 | <1 |
| Comparative example 1 | 5400 | 11.87 | 0.077 | <1 |
| Comparative example 2 | 14000 | 9.8 | 0.068 | <1 |
| Comparative example 3 | 31000 | 3.43 | 0.014 | <1 |

Based on the results in table 1 for the caprolactam prepared by Examples 1 to 3, all PM numbers were more than 20000 seconds, and extinction values (at wavelength of 290 nm) were less than 0.05, PAN numbers were less than 5, and chroma value was less than 1. All of the results indicated the compliance with the quality requirements in the industry. In contrast, the PM numbers of the caprolactam prepared by Comparative examples 1 and 2 were less than 20000 seconds, all PAN numbers of the caprolactam prepared by Comparative examples 1 to 3 were more than that of Examples 1 to 3, and the extinction values (at 290 nm wavelength) of the caprolactam prepared by Comparative examples 1 and 2 were more than 0.05. Accordingly, the caprolactams prepared by Comparative examples 1 to 3 did not satisfy the industry requirements in term of the requirements for PM number, PAN number and extinction value. The caprolactam prepared in Examples 1 to 3 indeed possessed the high quality required in the industry.

In addition, the caprolactam prepared by Example 1 was measured by gas chromatograph (HP6890) with a column of EQUITY™ 701 CUSTOM CAPILLARY COLUMN (Length 50M×I.D 0.53 μm×film thickness 2.0 μm), a column flow rate of 6.0 ml/min. The column was maintained at a column temperature of 80° C. for 8 minutes. Then the temperature was increased to 170° C. with the incremental rate of 20° C./minute, and the temperature was kept at 170° C. for 10 minutes to be analyzed using flame ionization detector (FID) at 250° C. The results do not show the production of cyclohexane, cyclohexene or cyclohexadiene and other substances. Besides simplifying the manufacturing process and reducing energy consumption significantly, the present disclosure also enhances the yield and obtains a high quality caprolactam.

It should be noted that all the drawings depict a structure, proportion, size, etc., are only used to indicate the disclosure of the specification for a person skilled in the art to understand and read. It is not intended to limit the conditions that can be implemented in the present disclosure and thus it does not have substantial technical meanings. Any modification of the structure, change of the proportion, or adjustment of the size will be within the scope encompassed in the technical contents disclosed in the present disclosure without departing from the spirit of the present disclosure.

What is claimed is:

1. A method for preparing caprolactam, comprising steps of:
    (a) subjecting cyclohexanone oxime and sulfuric acid to a Beckmann rearrangement reaction to obtain a rearrangement mixture;
    (b) neutralizing the rearrangement mixture with a base to obtain a first crude caprolactam solution rich in caprolactam and a second crude caprolactam solution rich in sulfate;
    (c) extracting at least the first crude caprolactam solution with an organic solvent to obtain a caprolactam organic solution;
    (d) mixing the caprolactam organic solution with hydrogen to perform a hydrogenation reaction in a hydrogenation reactor having a hydrogenation catalyst, wherein a weight hourly space velocity of the caprolactam organic solution is 1 to 20 per hour, a feeding hydrogen flow rate is $NM^3$ 0.01 to 0.15 $NM^3$ per hour per cubic meter of the caprolactam organic solution, and a hydrogen gauge pressure of an outlet of the hydrogenation reactor is 3 $kg/cm^2$ to 20 $kg/cm^2$; and
    (e) purifying the hydrogenated caprolactam organic solution, wherein the purification includes steps of evaporation and distillation to separate the caprolactam.

2. The method according to claim 1, further comprising extracting the second crude caprolactam solution with the organic solvent to obtain the caprolactam organic solution.

3. The method according to claim 2, wherein the first crude caprolactam solution and the second crude caprolactam solution are extracted with the organic solvent simultaneously.

4. The method according to claim 1, wherein the organic solvent is an aromatic hydrocarbon or a halogenated hydrocarbon.

5. The method according to claim 4, wherein the organic solvent is toluene, benzene or dichloroethane.

6. The method according to claim 1, wherein the base is ammonia.

7. The method according to claim 1, further comprising, after step (c), adjusting the electric conductivity of the caprolactam organic solution to 5 μmoh/cm to 100 μmoh/cm with a base aqueous solution.

8. The method according to claim 1, further comprising, after step (c), removing at least a portion of the organic solvent.

9. The method according to claim 1, wherein the hydrogenation catalyst comprises a carrier and an active metal carried on the carrier, and wherein the carrier is one selected from the group consisting of alumina, carbon and silica.

10. The method according to claim 9, wherein the active metal is one selected from the group consisting of ruthenium, rhodium, palladium, platinum and nickel.

11. The method according to claim 9, wherein an amount of the active metal is 5 wt % to 85 wt %.

12. The method according to claim 1, wherein the reaction temperature of the hydrogenation reaction is 50° C. to 180° C.

13. The method according to claim 1, further comprising, prior to step (e) or during step (e), adding at least one alkali metal hydroxide in the hydrogenated caprolactam organic solution.

14. The method according to claim 13, wherein the alkali metal hydroxide is at least one selected from the group consisting of sodium hydroxide and potassium hydroxide.

15. The method according to claim 13, wherein an amount of the alkali metal hydroxide is no more than 20 milliequivalent of the alkali metal hydroxide per kilogram of the hydrogenated caprolactam organic solution.

\* \* \* \* \*